US007395694B2

(12) United States Patent  (10) Patent No.: US 7,395,694 B2
Leinemann et al. (45) Date of Patent: Jul. 8, 2008

(54) SYSTEM AND METHOD FOR DETERMINING AN AIR CONTENT, AIR RELEASE ABILITY AND FOR FOAM FORMING ON OIL SURFACES

(75) Inventors: Magnus Leinemann, München (DE); Arthur Wetzel, Friedrichshafen (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 206 days.

(21) Appl. No.: 10/532,508

(22) PCT Filed: Oct. 22, 2003

(86) PCT No.: PCT/EP03/11684

§ 371 (c)(1), (2), (4) Date: Jul. 27, 2005

(87) PCT Pub. No.: WO2004/038386

PCT Pub. Date: May 6, 2004

(65) Prior Publication Data

US 2006/0162430 A1 Jul. 27, 2006

(30) Foreign Application Priority Data

Oct. 26, 2002 (DE) .................... 102 49 957

(51) Int. Cl.
*G01N 9/00* (2006.01)
(52) U.S. Cl. .................................... 73/32 R
(58) Field of Classification Search ............ 73/53.06, 73/53.05, 19.01, 19.11, 32 R
See application file for complete search history.

(56) References Cited

U.S. PATENT DOCUMENTS 3,232,097 A * 2/1966 Childs et al. .................. 137/7

(Continued)

FOREIGN PATENT DOCUMENTS

DE 25 51 260 5/1977

(Continued)

OTHER PUBLICATIONS

Zander, Von R., P. Rupprath, G. M. Schneider & E. Rohne, "Neue Labormeßmethode zur Beurteilung des Luftabscheideverhaltens von Fluiden", *Tribologie & Schmierungstechnik*, 42, May 1995, pp. 263-268.

(Continued)

*Primary Examiner*—Hezron E. Williams
*Assistant Examiner*—Rodney T Frank
(74) *Attorney, Agent, or Firm*—Davis Bujold & Daniels, P.L.L.C.

(57) ABSTRACT

This invention concerns a device (1) for the determination of air content, the air separation behavior and the surface foam formation of oils, in particular of transmission oils with an air-oil mixer (2) and a differential pressures sensor (3). A conveyor system (4) transports the oil through pipe lines (5) of the air-oil mixer (2). A compressed air port (6) is provided, which transports air into the pipe lines (5), of the air-oil mixer (2). A Venturi pipe (9) is installed in one of the pipe lines (5), and the differential pressure sensor (3) records, through at least two separate drill tubes (7, 8) in the conveyor system of the oil at the Venturi pipe (9), differential pressures in the oil.

14 Claims, 1 Drawing Sheet

U.S. PATENT DOCUMENTS

| | | | |
|---|---|---|---|
| 5,243,848 A * | 9/1993 | Cox et al. | 73/19.05 |
| 5,375,459 A * | 12/1994 | Gerke et al. | 73/60.11 |
| 5,406,828 A * | 4/1995 | Hunter et al. | 73/1.62 |
| 5,423,226 A * | 6/1995 | Hunter et al. | 73/861.63 |
| 5,465,610 A | 11/1995 | Loisel | |
| 5,648,601 A * | 7/1997 | Katoh et al. | 73/1.06 |
| 5,965,805 A * | 10/1999 | Watts et al. | 73/53.01 |
| 6,612,187 B1 * | 9/2003 | Lund | 73/861.04 |

FOREIGN PATENT DOCUMENTS

| | | |
|---|---|---|
| DE | 34 33 017 A1 | 3/1986 |
| DE | 692 04 165 T2 | 4/1996 |
| DE | 40 36 344 C2 | 11/1997 |
| DE | 197 40 095 C2 | 6/2000 |
| DE | 199 49 922 C1 | 5/2001 |
| FR | 2 670 894 | 6/1992 |
| GB | 2 081 896 A | 2/1982 |

OTHER PUBLICATIONS

Zander, Von R., P. Rupprath, G. M. Schneider, E. Rohne & J. Brandt. "Neue Labormethode zur Beurteilung des Schaumverhaltens von Fluiden", *Tribologie & Schmierungstechnik,* 49, Jan. 2002, pp. 30-37.

* cited by examiner

SYSTEM AND METHOD FOR DETERMINING AN AIR CONTENT, AIR RELEASE ABILITY AND FOR FOAM FORMING ON OIL SURFACES

This application is a national stage completion of PCT/EP filed which claims priority from German Application Serial No. filed.

FIELD OF THE INVENTION

The invention concerns a device for determination of the air content, the air separation behavior and the surface area foam formation of oils, and a procedure for operating a device for regulation of the air content, the air separation behavior and the surface area foam formation of oils, in particular, both related to transmission oil.

BACKGROUND OF THE INVENTION

Oil and air dispersions in the transmission oil lead to worsened efficiencies of transmissions and can, in extreme cases, lead to oil leakages. The ability of the oil to quickly separate incorporated air is, therefore, an important quality criterion, and measuring systems to determine the air separating behavior (LAV) of oils is thus a result of great importance.

The Castrol company is known to have a device to determine air separation behavior of oils with an air-oil mixer and a differential pressure sensor. The air-oil mixer shows a container that can partially be filled with oil. This container has a glass cover and a propeller that is only lightly dipped in the oil. The propeller can be raised up to 10,000 revs/min and thus swirls the oil. With the aid of two superimposed pressure measuring points, different hydrostatic pressures are then determined from their difference in the air content of the oil. Unfavorable to this state of the art technique is the high cost, which is not suited well in practice, due to the high measuring technology that accurately manufactured pressure connections and very finely triggered differential pressure sensors will need so that small differences of pressure can be distinguished. Rotating oil puts additional pressure on the measuring points for this state of the art technique. Thus, the sample must first be brought to rest after the air entry which leads to delayed measurement recording. Such LAV measuring systems do not, therefore, correlate completely with the situation in the transmission.

The purpose of the invention is to create a device for determination of the air content, the regulation of the air separation behavior and the surface area foam formation of oils, in particular related to transmission oils, with earlier recording of measurement values and a practical procedure for operating a device for regulation of the air content, the air separation behavior and the surface area foam formation of oils, in particular related to transmission oils, with earlier indication of measurement values recorded.

The solution follows with a device for the determination of the air content, the air separation behavior and the surface area foam formation of oils, in particular, related to transmission oil and procedure for operating a device for regulation of the air content, the air separation behavior and the surface area foam formation of oils, in particular, related to transmission oil.

SUMMARY OF THE INVENTION

In accordance with the invention, a device is provided for the determination of the air content, the air separation behavior and the surface area foam formation of oils, in particular related to transmission oils, with an air-oil mixer and a differential pressure sensor. A conveyor system is intended, which transports the oil through pipe lines of the air-oil mixer. The differential pressure sensor covers at least 2 separate drill tubes that lead to a Venturi pipe of differential pressures in the oil. The Venturi pipe produces differential pressures, due to changes in cross-sectional square area, that are proportional for the respective density of the oil. If the flow rate in the Venturi pipe is known and the current flows without elevation changes, then, from the measured difference in pressure, the densities of the oil can be determined and thus the air content. The flow rate results from the adjusted volume flow to the conveyor system and the cross-section conditions in the Venturi pipe. An advantage of the device according to the invention follows from the early recording of measurement values, with which enrichment of the oil with air results from continuous mixing, and thus the condition of the transmission is realistically detected. The more time that passes between air entry and measurement of the enrichment of the oil with air, the more off from the true value the measured values are. A further advantage of the device according to invention is the ability to detect small measurement volumes that are commonly found in oil samples and from transmission and field tests. In addition, with a device according to this invention, a substantially larger measuring range for the differential pressure results, and thus the measuring technology resolution is more easily feasible. With measurement of the differential pressure at repeated time intervals, the change of the density of the oil, that is, its variable air content and thus the air separation behavior, can be determined.

In addition, the volume of the surface foam (ml) can be measured by means of a container (glass ball).

In accordance with a preferential arrangement of the invention, the compressed air port is controllable, so that the supply of air can be shut off. A mixer is provided to intensively mix the air with the oil in the pipe lines.

In accordance with another preferential arrangement of the invention, there is at least one separator in the form of a volume container in the pipe lines, so that with opened air supply and high air surplus of approximately 6 l/min in 200 ml of oil, larger bubbles can be separated before the measuring section in the Venturi pipe. This is especially the case for large bubbles with a circumference of over 4 mm, which otherwise could lead to faulty measurements of the differential pressures, if, for example, an air bubble just passes the measuring point in the Venturi pipe and finds itself at the measuring point before dispersion, which would lead to large changes in differential pressures and would prevent stable measured values in the long term.

In accordance with a further preferential arrangement of the invention, the separator exhibits a diameter of approximately 20 mm or preferably approximately 30 mm.

In accordance with a further preferable arrangement of the invention, the air-oil mixer is provided with a receptacle for surface foam.

In accordance with a further preferential arrangement of the invention, a temperature-regulated container is provided, having an aluminum plate at the front side, for the purpose of variable testing temperatures, and the air-oil mixers and the pipe lines can be arranged with the Venturi pipe in the temperature-regulated container in such a way that the measuring cycle can be kept at the right temperature by an oil bath.

In accordance with a further preferential arrangement of the invention, a circulating thermostat is installed to the temperature-regulated container, that can keep the oil bath in the container up to 200° C.

In accordance with a further preferential arrangement of the invention, a A/D converter map and a calculator are provided, and the differential pressure receivers are connected by the A/D converter map with the calculator, so that the measurements can take place automatically.

In accordance with a further preferential arrangement of the invention, the conveyor system is installed with a gear pump that has a maximum flow rate of 3,607 ml/min and maintains thermal stability up to 130° C.

According to the invention, there is a procedure for the determination of the air content at different volume flows with the device according to the invention characterized by the pouring of preferably 150 ml of the oil being tested by the volume container into the air-oil mixer, switching on a water jet pump, so that oil is sucked into hoses and/or into the vision panel above a measuring cell of the differential pressure receiver, preventing the back flow of the oil into the hoses above the measuring cell, switching on the conveyor system, filling up with more of the oil being tested until the pipe lines of the air-oil mixer are full without bubbles developing, adjustment of the air supply, and setting of the conveyor system to maximum flow (i.e., at 3,400 ml/mm), transfer of the oil being tested and measuring of the differential pressure after 7 minutes of air supply.

In accordance with the invention, the procedure for the determination of the air separation behavior with the device according to the invention is characterized by the pouring of preferably 150 ml of the oil being tested by the volume container into the air-oil mixer, switching on a water jet pump, so that oil is sucked into hoses and/or into the vision panel above a measuring cell of the differential pressure receiver, preventing the back flow of the oil into the hoses above the measuring cell, switching on the conveyor system, filling up with more of the oil being tested until the pipes lines of the air-oil mixer are full without bubbles developing, setting the conveyor system to a certain flow for 7 minutes with sucking up of air, measurements of the differential pressures, stopping the air supply, time measurement and measurement of the respective differential pressures at regular intervals.

In accordance with the invention, a further procedure for the determination of the air separation behavior with the device according to the invention is characterized by the pouring of preferably 150 ml of the oil being tested through a filler funnel into the air-oil mixer, switching on a water jet pump, so that oil is sucked into hoses above a measuring cell of the differential pressure sensor, preventing the back flow of the oil into the hoses above the measuring cell, switching on the conveyor system, filling up with more of the oil being tested until the pipe lines of the air-oil mixer are full without bubbles developing, adjustment of the air supply, should the occasion arise through two pin valves, setting the conveyor system to a certain flow for 7 minutes, measurements of the differential pressures, stopping the air supply, time measurement and measurement of the respective differential pressures at regular intervals.

In accordance with a further arrangement of the procedure according to invention, the temperature of the oil being tested will be adjusted approximately 20° C. higher than the set thermostat, defined at 90° C. and 130° C.

BRIEF DESCRIPTION OF THE DRAWING

The invention will now be described, by way of example, with reference to the accompanying drawings in which.

DETAILED DESCRIPTION OF THE INVENTION

Figure 1:
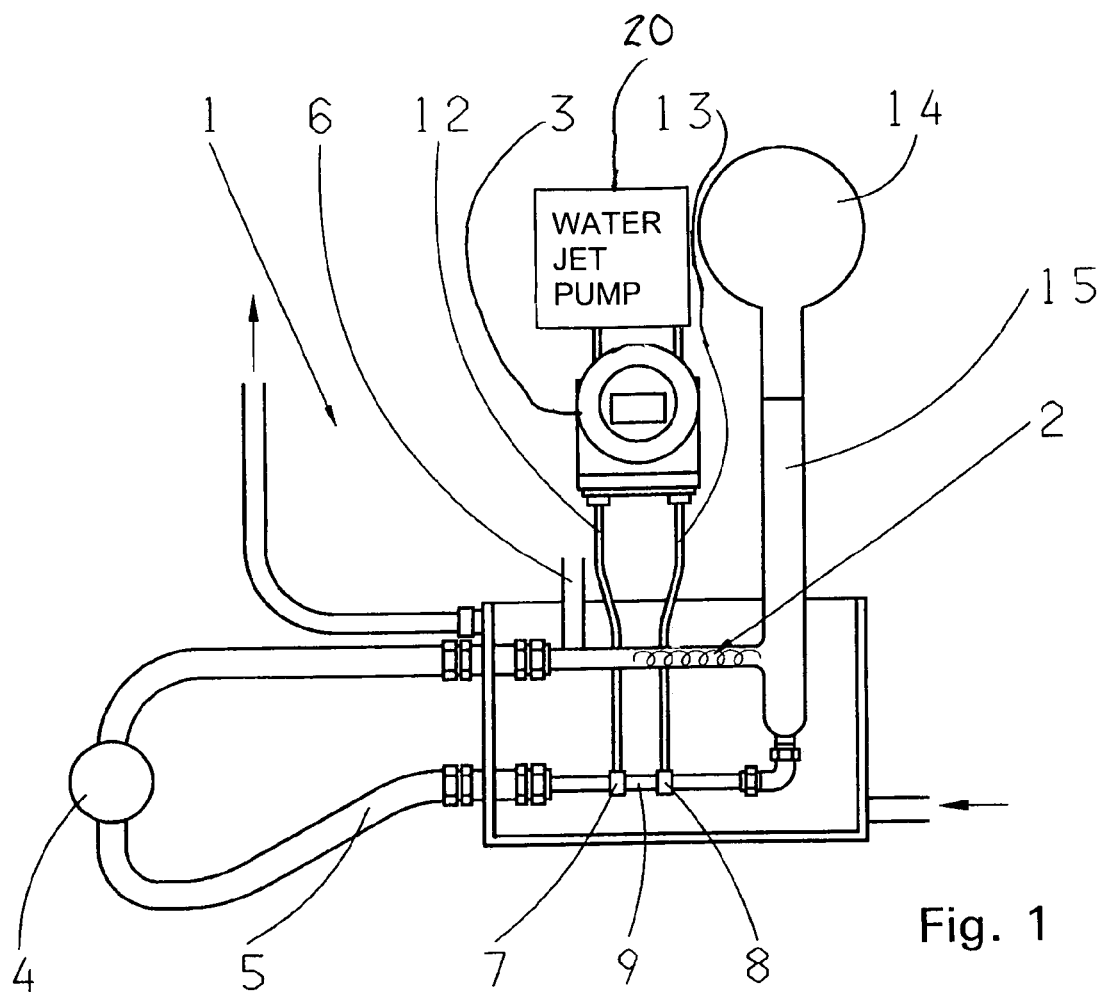
FIG. 1 is a display of the front of the device in accordance with the invention.
Figure 2:
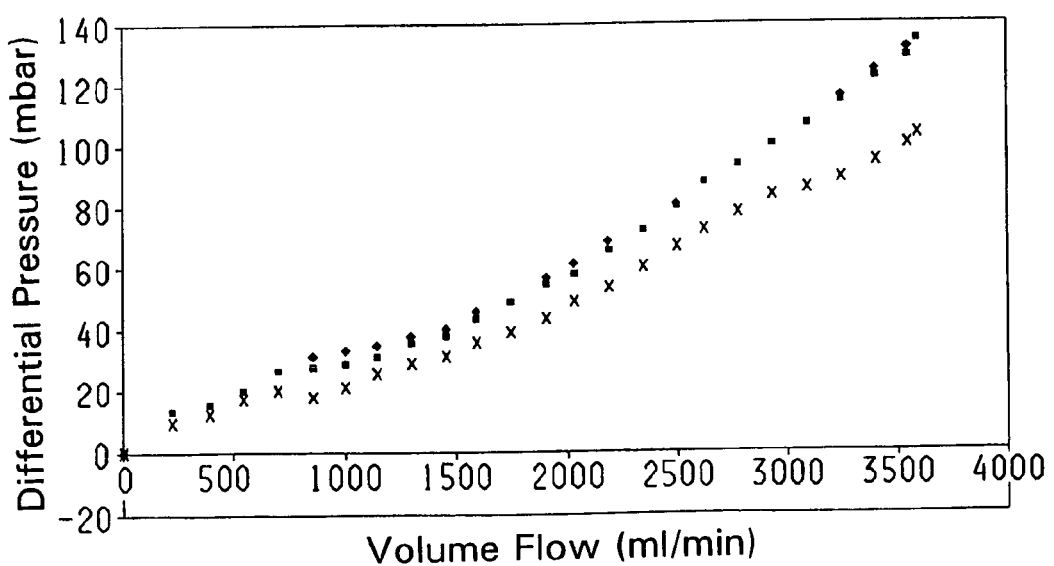
FIG. 2 is a diagram with the device in accordance with the invention recording differential pressures for an oil being tested.

FIG. 1:

A device 1 for the determination of the air separation behavior of transmission oils is provided with an air-oil mixer 2 and a differential pressure sensor 3. A facilitative mechanism 4 is provided as a gear pump with a maximum flow rate of 3,607 ml/min and thermal stability up to 130° C., which sucks the oil through pipe lines 5 of the air-oil mixer 2.

All metal-manufactured parts of the device 1 are made of V2 A high-grade steel. All parts such as seals, hoses, etc., are made of PTEE or FKM. This material is also used for the pump head of the gear pump. There are no silicon-based materials. Glass that can resist temperatures of up to 150° C., such as Duran glass, is used in manufacturing the air-oil mixer 2.

A compressed air port 6 directs air through pin valves (not represented) into the pipe lines 5 of the air-oil mixer 2. The compressed air port 6 is controllable, so that the air intake can be turned off. The differential pressure sensor 3 absorbs differential pressures in the oil through two separate drill tubes 7, 8 in the conveyor system of the oil, to a Venturi pipe (9) and through hoses (12, 13. A mixer (not represented) is intended for intensive mixing of air with the oil in the pipe lines 5.

An off switch 15 in the form of a volume container is installed in the pipe lines 5, so that, at open air supply and high air surplus of about 6 l/min of air in 150 ml of oil, larger bubbles can be separated before the measuring section in the Venturi pipe 9. The separator 15 exhibited a diameter of 30 mm. The air-oil mixer 2) is provided with a receptacle 14.

For variable testing temperatures, a container is constructed with a temperature-regulated container that has an aluminum plate at the front side and the air-oil mixer 2, and the pipe lines 5 can be arranged with the Venturi pipe 9 in the temperature-regulated container (not represented) in such a way that the measuring cycle can be kept at the right temperature over an oil bath in the temperature-regulated container. A circulating thermostat is provided for the temperature-regulated container, that can heat the oil bath in the container up to 200° C. An A/D converter map (not represented) and a calculator 12 are connected to the differential pressure sensor 3, so that the measurements can take place automatically.

Procedures for the Operation of Device 1:

A procedure for the determination of the air content with constant flow rates with the device 1 takes place by pouring 150 ml of the oil being tested oil by the volume container into the air-oil mixer 2, switching on a water jet pump 20, so that oil is sucked into hoses and/or in the vision panel 12, 13 above a measuring cell of the differential pressure sensor 3. The back flow of the oil into the hoses (12, 13) is prevented by closing the spigot. Then there follows switching on the conveyor system 4, filling up with more of the oil being tested until the pipe lines of the air-oil mixer is full without bubbles developing, adjustment of the air supply, and setting of the conveyor system at 3,400 ml/min. Transfer of the oil being tested and measurement of the differential pressure lasts 7 minutes, and then the display of the differential receptor will be recorded.

The conveyor system 4) sucks the oil being tested in a clockwise direction through the pipe lines 5 and can pump with air inlet, so that separate regulating of the air supply is not needed.

In particular, large bubbles are separated in the separator 15 from the flow volume of the oil being tested to improve the measuring accuracy.

Before evaluation of the measurements, the device 1 is preferably calibrated with water, whereby at least two measuring series are ascertainable with a fitting function that can be used on the analysis algorithm. The fitting function can be improved with more than two series of measurements.

For the determination of air contents at different volume flows, the oil being tested should be set at the maximum volume flow for 7 minutes and transferred with opened air supply, and then the first measurement can be recorded and subsequently all regulating volume flows can be measured in a timely manner. Thus, in addition to the differential pressures, the temperature of the oil being tested can also be recorded.

For the determination of the air contents at variable temperatures, the volume flow should be kept constant. The temperature of the oil being tested will be set at approximately 20° C. higher than the set thermostat in the container.

For the determination of the air separation behavior, the oil being tested is mixed for 7 minutes at open air supply, and afterwards the differential pressure is recorded and the air supply is stopped. Then the time measurement begins, and the differential pressure is recorded at regular intervals.

FIG. 2:

As a function of the adjusted volume flow, the differential pressures recorded by the device 1 are shown in the upper dotted line for an oil being tested with defoamer and in the lower dotted line without defoamer.

REFERENCE NUMERALS

1 Device
2 Air-oil mixer
3 Differential pressure sensor
4 Conveyor system
5 Pipe lines
6 Compressed air port
7 Drill tubes
8 Drill tubes
9 Venturi pipe
12 Hoses
13 Hoses
14 Receptacle
15 Separator

The invention claimed is:

1. A device (1), for determining the density and air content of an oil sample, the device comprising:
   an oil circuit comprising:
      a pump (4) and pipe lines (5) for conducting the oil sample through the oil circuit;
      an air delivery port (6) for introducing air into the oil circuit;
      an air-oil mixer (2) where the air mixes with the oil;
      a venturi pipe (9);
      a first oil pressure sampling orifice on an upstream side of the venturi pipe and a second oil pressure sampling orifice on a downstream side of the venturi pipe;
   a differential pressure sensor (3) connected to the first and second oil sampling orifices; and
   wherein the oil sample is delivered to the venturi pipe at a known flow rate, a pressure differential of the oil sample across the venturi pipe (9) is measured by the differential pressure sensor (3) connected with the first and second oil pressure sampling orifices and, based on the known flow rate of the oil sample through the venturi pipe (9) the density of the oil sample is proportionally determined from the pressure differential across the venturi pipe and consequently the air content of the oil is determined.

2. The device (1) according to claim 1, wherein the air delivery port (6) is controllable, and the air-oil mixer (2) is installed for turbulent mixing of the air with the oil in the pipe lines (5).

3. The device (1) according to claim 1, wherein the oil circuit further comprises at least one separator (15) upstream of the venturi pipe (9) for separating larger air bubbles from the oil sample.

4. The device (1) according to claim 3, wherein a diameter of the separator (15) is approximately 20 to 30 mm.

5. The device (1) according to claim 1, wherein the air-oil mixer (2) is partially manufactured of glass.

6. The device (1) according to claim 1, wherein the air-oil mixer (2) is equipped with a receptacle (14) for surface foam.

7. The device (1) according to claim 1, wherein the air-oil mixer (2) and the pipe lines connected to the venturi pipe (9) are arranged within a temperature regulating container.

8. The device (1) according to claim 7, wherein the temperature-regulating container has a circulating thermostat.

9. The device (1) according to claim 1, wherein the device further comprises an A/D converter map and a calculator and the differential pressure sensor (3) is connected with the A/D converter map and the calculator.

10. The device (1) according to claim 1, wherein the pump is a gear pump.

11. A device (1), for determining the density and air content of an oil sample as well as the separation behavior of the oil sample over time, the device comprising:
   an oil circuit comprising:
      pipe lines (5) for conducting the oil sample through the oil circuit;
      a compressed air delivery port for introducing air into the oil circuit;
      an air-oil mixer (2) where the air mixes with the oil sample;
      a venturi pipe (9);
      a first oil pressure sampling orifice on an upstream side of the venturi pipe and a second oil pressure sampling orifice on a downstream side of the venturi pipe;
   a differential pressure sensor (3) connected to the first and second oil sampling orifices;
   the oil sample is delivered to the venturi pipe at a known flow rate, a pressure differential of the oil sample across the venturi pipe (9) is measured by the differential pressure sensor (3) connected with the first and second oil pressure sampling orifices and, based on the known flow rate of the oil sample through the venturi pipe (9) the density of the oil sample is proportionally determined from the pressure differential across the venturi pipe and consequently the air content of the oil is determined; and
   wherein the compressed air delivery port is closed to stop the introduction of air into the oil sample, and a plurality of differential pressures across the venturi pipe (9) are recorded at regular time intervals to determine the separation behavior of the oil sample.

12. A method for determining the density and air content of an oil sample with a device having an oil circuit comprising a pump and pipe lines (5) for conducting the oil sample through the oil circuit, an air delivery port for introducing air into the oil circuit an air-oil mixer (2) where the air mixes with the oil sample, a venturi pipe (9), a first oil pressure sampling orifice on an upstream side of the venturi pipe and a second oil pressure sampling orifice on a downstream side of the venturi pipe, a differential pressure sensor (3) connected to the first and second oil sampling orifices, the method comprising the steps of:

introducing the oil sample into the pipe lines of the oil circuit;

introducing air into the oil circuit and mixing the air with the oil sample in the air-oil mixer (2);

delivering the air and oil sample to the venturi pipe at a known flow rate;

measuring a pressure differential of the mixed air and oil sample across the venturi pipe (9) according to the differential pressure sensor (3) connected with the first and second oil pressure sampling orifices; and using the measured pressure differential across the venturi pipe to determine the proportionally related density of the mixed air and oil sample according to the known flow rate of the mixed air and oil sample through the venturi pipe (9) and consequently determining the air content of the oil.

13. A method for determining the density and air content as well as the separation characteristics of an oil sample with a device having an oil circuit comprising a pump and pipe lines (5) for conducting the oil sample through the oil circuit, a compressed air delivery port for introducing air into the oil circuit, an air-oil mixer (2) where the compressed air mixes with the oil sample, a venturi pipe (9), a first oil pressure sampling orifice on an upstream side of the venturi pipe and a second oil pressure sampling orifice on a downstream side of the venturi pipe, a differential pressure sensor (3) connected to the first and second oil sampling orifices, the method comprising the steps of:

introducing oil sample into the pipe lines of the oil circuit;

introducing air into the oil circuit and mixing the air with the oil sample in the air-oil mixer (2);

delivering the air oil sample to the venturi pipe at a known flow rate;

measuring a pressure differential of the mixed air and oil sample across the venturi pipe (9) according to the differential pressure sensor (3) connected with the first and second oil pressure sampling orifices;

using the measured pressure differential across the venturi pipe to determine the proportionally related density of the mixed air and oil sample according to the known flow rate of the mixed air and oil sample through the venturi pipe (9) and consequently determining the air content of the oil; and stopping the introduction of air into the oil sample, and recording a plurality of differential pressures across the venturi pipe (9) at regular time intervals to determine the separation characteristics of the oil sample.

14. A method for determining the density and air content as well as the separation characteristics and foam formation of an oil sample with a device having an oil circuit comprising a pump and pipe lines (5) for conducting the oil sample through the oil circuit, an air delivery port for introducing air into the oil circuit, an air-oil mixer (2) where the air mixes with the oil sample, a venturi pipe (9), a first oil pressure sampling orifice on an upstream side of the venturi pipe and a second oil pressure sampling orifice on a downstream side of the venturi pipe, a differential pressure sensor (3) connected to the first and second oil sampling orifices, the method comprising the steps of:

introducing the oil sample into the pipe lines of the oil circuit;

introducing air into the oil circuit and mixing the air with the oil sample in the air-oil mixer (2);

delivering the air oil sample to the venturi pipe at a known flow rate;

measuring a pressure differential of the mixed air and oil sample across the venturi pipe (9) according to the differential pressure sensor (3) connected with the first and second oil pressure sampling orifices;

using the measured pressure differential across the venturi pipe to determine the proportionally related density of the mixed air and oil sample according to the known flow rate of the mixed air and oil sample through the venturi pipe (9) and consequently determining the air content of the oil;

stopping the introduction of air into the oil sample, and recording a plurality of differential pressures across the venturi pipe (9) at regular time intervals to determine the separation characteristics of the oil sample; and collecting any surface foam of the mixed air and oil sample in a container connected with the oil circuit and measuring a collected volume of the surface foam in the container.

\* \* \* \* \*